United States Patent
Lin et al.

(10) Patent No.: US 11,793,842 B2
(45) Date of Patent: Oct. 24, 2023

(54) **METHOD FOR REDUCING INFLAMMATION OF CHONDROCYTES CAUSED BY URIC ACID CRYSTALS USING *LACTOBACILLUS PLANTARUM* TCI227**

(71) Applicant: TCI CO., LTD., Taipei (TW)

(72) Inventors: Yung-Hsiang Lin, Taipei (TW); Chu-Han Huang, Taipei (TW); Cheng-Yu Ho, Taipei (TW)

(73) Assignee: TCI CO., LTD., Taipei (TW)

( * ) Notice: Subject to any disclaimer, the term of this patent is extended or adjusted under 35 U.S.C. 154(b) by 58 days.

(21) Appl. No.: 17/543,752

(22) Filed: Dec. 7, 2021

(65) Prior Publication Data

US 2022/0088095 A1 Mar. 24, 2022

Related U.S. Application Data

(62) Division of application No. 16/693,758, filed on Nov. 25, 2019, now abandoned.

(30) Foreign Application Priority Data

Jul. 3, 2019 (TW) .................................. 108123471

(51) Int. Cl.
*A01N 63/00* (2020.01)
*A61K 35/747* (2015.01)
*A61P 19/06* (2006.01)
*C12N 1/20* (2006.01)
*C12R 1/25* (2006.01)

(52) U.S. Cl.
CPC ............ *A61K 35/747* (2013.01); *A61P 19/06* (2018.01); *C12N 1/205* (2021.05); *C12R 2001/25* (2021.05)

(58) Field of Classification Search
CPC .................................................. A61K 35/747
See application file for complete search history.

(56) References Cited

U.S. PATENT DOCUMENTS

2013/0330299 A1* 12/2013 Ranganathan ......... A61K 45/06
424/93.3

FOREIGN PATENT DOCUMENTS

KR 20130046896 A * 5/2013

* cited by examiner

*Primary Examiner* — Albert M Navarro
(74) *Attorney, Agent, or Firm* — Chieh-Mei Wang

(57) ABSTRACT

The present disclosure provides a method for regulating expression of IL-1β gene, MMP1a gene and TIMP1 gene of chondrocytes using a *Lactobacillus plantarum* strain TCI227.

5 Claims, 6 Drawing Sheets

Specification includes a Sequence Listing.

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
ttgggcctca aggaaagaa                                             20

<210> SEQ ID NO 2
<211> LENGTH: 23
<212> TYPE: DNA
<213> ORGANISM: Artificial Sequence
<220> FEATURE:
<223> OTHER INFORMATION: synthetic primer

<400> SEQUENCE: 2
tgtgaggtgc tgatgtacca gtt                                        23

<210> SEQ ID NO 3
<211> LENGTH: 17
<212> TYPE: DNA
<213> ORGANISM: Artificial Sequence
<220> FEATURE:
<223> OTHER INFORMATION: synthetic primer

<400> SEQUENCE: 3
cccaaggcgc cacatct                                               17

<210> SEQ ID NO 4
<211> LENGTH: 23
<212> TYPE: DNA
<213> ORGANISM: Artificial Sequence
<220> FEATURE:
<223> OTHER INFORMATION: synthetic primer

<400> SEQUENCE: 4
caccccgaag ttcagtagac aga                                        23

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5
gggcaaaaac atgcaagcta a                                          21

<210> SEQ ID NO 6
<211> LENGTH: 24
<212> TYPE: DNA
<213> ORGANISM: Artificial Sequence
<220> FEATURE:
<223> OTHER INFORMATION: synthetic primer

<400> SEQUENCE: 6
gtgttttggt acgaggattg ttgt                                       24

<210> SEQ ID NO 7
<211> LENGTH: 21
<212> TYPE: DNA
<213> ORGANISM: Artificial Sequence

```
<220> FEATURE:
<223> OTHER INFORMATION: synthetic primer

<400> SEQUENCE: 7
gcctaaggaa cggaaatttg c                                            21

<210> SEQ ID NO 8
<211> LENGTH: 19
<212> TYPE: DNA
<213> ORGANISM: Artificial Sequence
<220> FEATURE:
<223> OTHER INFORMATION: synthetic primer

<400> SEQUENCE: 8
agcccacgag gacctgatc                                               19
```

US 11,793,842 B2

METHOD FOR REDUCING INFLAMMATION OF CHONDROCYTES CAUSED BY URIC ACID CRYSTALS USING *LACTOBACILLUS PLANTARUM* TCI227

CROSS-REFERENCE TO RELATED APPLICATION

This application is a division of U.S. patent application Ser. No. 16/693,758, filed on Nov. 25, 2019, which claims priority to Taiwan patent application No. 108123471, filed on Jul. 3, 2019, the entirety of which are incorporated herein by reference.

REFERENCE OF AN ELECTRONIC SEQUENCE LISTING

The contents of the electronic sequence listing (P200725USI-D1_ST25.txt; Size: 1.7 KB; and Date of Creation: Dec. 3, 2021) is herein incorporated by reference in its entirety.

BACKGROUND OF THE INVENTION

1. Field of the Invention

The present invention relates to a method of a *Lactobacillus plantarum* strain TCI227 for regulating expression of IL-1β gene, MMP1a gene and TIMP1 gene of chondrocytes.

2. The Prior Art

Gout, also known as hyperuricemia, is mainly a purine metabolic disorder. When the human body cannot metabolize purine from the human body, the purine in the body would further oxidize to form uric acid. The uric acid would deposit in the joints in the form of sodium salts, causing the immune system in the body to overreact and cause inflammation. In recent years, due to changes in eating habits, the intake of high purine foods and beer drinks has increased, leading to an increase in the incidence of gout, and the age of onset has also declined. In addition, there are more and more risk factors, such as metabolic syndrome. Longer life expectancy and dietary changes make the effects of gout more common.

Currently used drugs for the treatment of gout are drugs for inhibiting the production of uric acid, such as Allopurinol; drugs that promote uric acid excretion, such as Probenecid and Sulfinpyrazone; and drugs for reducing the frequency of gout attacks, such as Colchicine. However, the aforementioned drugs are known to have the risk of side effects such as skin allergic reactions, gastrointestinal discomfort, kidney damage, liver damage, and leukopenia.

In addition, most of the medicaments used to treat gout are made of chemical components. Long-term use is not only harmful to human health, but these products are often expensive and not affordable for the average user. In order to solve the above problems, those skilled in the art urgently need to develop novel medicaments or food products having the effects on relieving and treating gout for the benefit of a large group of people in need thereof.

SUMMARY OF THE INVENTION

A primary objective of the present invention is to provide a method for regulating expression of interleukin-1β (IL-1β) gene, matrix metallopeptidase 1a (MMP1a) gene, and TIMP metallopeptidase inhibitor 1 (TIMP1) gene of chondrocytes, comprising administering to a subject in need thereof a composition comprising an effective amount of a *Lactobacillus plantarum* strain.

According to an embodiment of the present invention, the expression of IL-1β gene and MMP1a gene is down-regulated, and the expression of TIMP1 gene is up-regulated.

According to an embodiment of the present invention, the effective amount of the *Lactobacillus plantarum* strain is at least $5 \times 10^8$ cells/mL.

According to an embodiment of the present invention, the *Lactobacillus plantarum* strain comprises an inactivated bacterium.

According to an embodiment of the present invention, the composition is a medicament or a food product.

According to an embodiment of the present invention, the *Lactobacillus plantarum* strain is deposited in Deutsche Sammlung von Mikroorganismen and Zellkulturen under an accession number DSM 33287.

In summary, the *Lactobacillus plantarum* strain has the effect on reducing the inflammatory reaction caused by uric acid crystals, lowering uric acid value, reducing the degree of joint swelling, and regulating expressions of IL-1β gene, MMP1a gene, and TIMP1 gene of chondrocytes.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
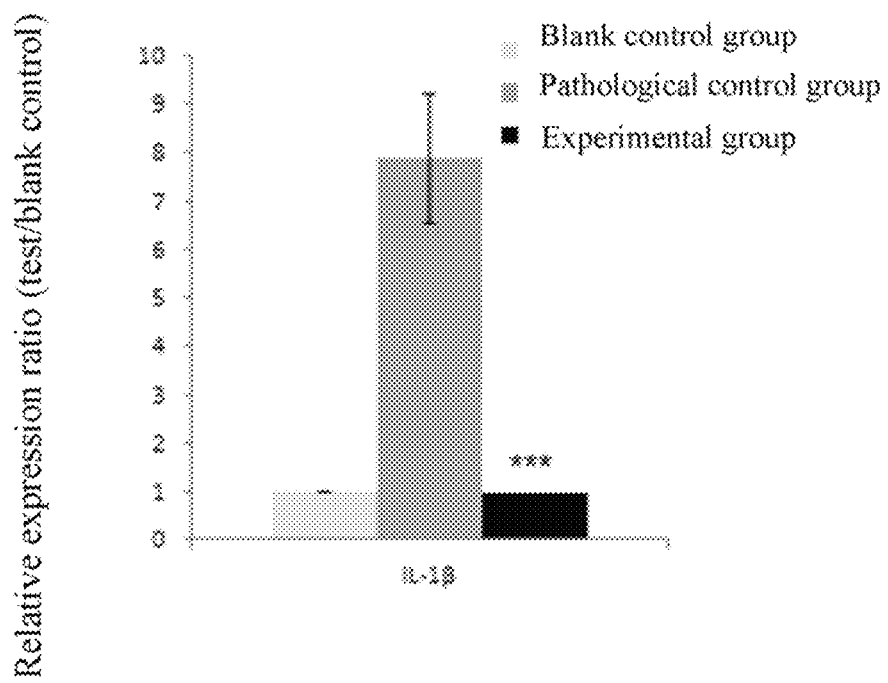
FIG. 1 is a schematic diagram showing the effect of the *Lactobacillus plantarum* strain TCI227 of the present invention on regulating the expression of the IL-1β gene, wherein "***" indicates when compared with the pathological control group, $p<0.001$.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Statistical analysis was performed using Excel. Data are expressed as mean±standard deviation (SD), and the difference between each group is analyzed by the Student's t-test.

According to the present invention, Lactobacillus plantarum is a Gram-positive anaerobic bacterium that grows at temperatures above 15° C. but not exceeding 45° C. and produces lactic acid.

As used herein, the term "treating" or "treatment" refers to alleviating, reducing, ameliorating, relieving, or controlling one or more clinical signs of a disease or disorder, and lowering, stopping, or reversing the progression of severity regarding the condition or symptom being treated.

According to the present invention, the medicament can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The medicament according to the present invention may be administered by a parenteral route selected from the group consisting of: intraperitoneal injection, subcutaneous injection, intramuscular injection and intravenous injection.

According to the present invention, the medicament may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, disintegrating agent, dispersing agent, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

According to the present invention, the food product can be used as a food additive, added by the conventional method in the preparation of the raw material, or added during the preparation of food, and prepared with any edible material into food products for human and non-human animals.

According to the present invention, types of food products include, but not limited to, beverages, fermented foods, bakery products, health foods, and dietary supplements.

Example 1

Evaluation of the Effect of Lactobacillus plantarum Strain TCI227 on Reducing Inflammatory Response Caused by Uric Acid Crystals It was investigated in this example whether the Lactobacillus plantarum strain TCI227 which was deposited in Deutsche Sammlung von Mikroorganismen und Zellkulturen (Address: Inhoffenstr. 7 B D-38124 Braunschweig, Germany) on Sep. 19, 2019, under an accession number DSM 33287, and deposited in Biosource Collection and Research Center (BCRC) of Food Industry Research and Development Institute (FIRDI) on Apr. 15, 2019, under an accession number BCRC 910884 can regulate the gene expression related to inflammation to reduce the inflammatory response caused by uric acid crystals.

First, the inactivated cells of the Lactobacillus plantarum strain TCI227 were prepared, and the preparation process was as follows: the Lactobacillus plantarum strain TCI227 of the present invention in the frozen bacterial culture preservation tube was activated by a single culture of the MRS medium. 1% of the activated bacterial solution was cultured in a new medium and cultured at 37° C. for 16 hours, and centrifuged at 10,000 rpm for 5 minutes. The medium was removed and washed with PBS, and this action was repeated 3 times. PBS was used to resuspend the bacteria as 1 OD suspension. The suspension was sterilized at 121° C. for 15 minutes to obtain TCI227 inactivated cells.

Mouse chondrocytes (ATDC5, purchased from the American Type Culture Collection (ATCC)) were cultured in Dulbecco's Modified Eagle's Medium (DMEM) and Ham's F12 medium (1:1) (supplemented with 2 mM glutamine and 5% fetal bovine serum (FBS)(Gibco)) in 6-well plates, and the cell concentration in 2 mL of the medium was $1 \times 10^5$ cells/well. After 24 hours of culture, new medium was replaced.

Thereafter, the cells were divided into three groups including one blank control group, one pathological control group, and one experimental group. Among them, the experimental group was treated by diluting the inactivated cells of Lactobacillus plantarum strain TCI227 into a dilution having a concentration of $5 \times 10^8$ cells/mL, and a $5 \times 10^8$ cells/mL dilution and 0.125 mg/mL uric acid crystals (monosodium urate, MSU) were added to the cells in the experimental group. The pathological control group was treated by adding 0.125 mg/mL uric acid crystals to the cells in the pathological control group, and the cells in the blank control group were added with medium. Each group of cells was cultured in an incubator for 24 hours, and then each group of cell cultures was collected and used for gene expression analysis.

In this example, genes for analyzing inflammation include the interleukin-1β (IL-1β) gene, the tumor necrosis factor-α (TNF-α) gene, the matrix metallopeptidase 1a (MMP1a) gene, and the TIMP metallopeptidase inhibitor 1 (TIMP1) gene.

RNA extraction was performed using an RNA extraction kit (Genemark). 2,000 ng of the RNA in each group thus obtained was taken and the extracted RNA was reverse transcribed into cDNA by SuperScript® III reverse transcriptase (Invitrogen). The cDNA was used as a template, primer pairs for amplification of target genes, including IL-1β, TNF-α, MMP1a, and TIMP1 were used, and their nucleotide sequences are shown in Table 1. The quantification of target genes was measured by quantitative real-time PCR using KAPA SYBR FAST qPCR kit (2×) (KAPA Biosystems) carried out in Step One Plus Real-Time PCR system (ABI). The melting curves of the PCR product were analyzed during the quantitative real-time PCR.

TABLE 1

| Target gene | SEQ ID NO.# | Primer name | Sequence (5'→3') | PCR product size (bp) |
|---|---|---|---|---|
| IL-1β | 1 | IL1B-F | TTGGGCCTCAAAGGAAAGAA | 200 |
|  | 2 | IL1B-R | TGTGAGGTGCTGATGTACCAGTT |  |
| TNF-α | 3 | TNFA-F | CCCAAGGCGCCACATCT | 200 |
|  | 4 | TNFA-R | CACCCCGAAGTTCAGTAGACAGA |  |
| MMP1α | 5 | MMP1a-F | GGGCAAAAACATGCAAGCTAA | 200 |
|  | 6 | MMP1a-R | GTGTTTTGGTACGAGGATTGTTGT |  |
| TIMP1 | 7 | TIMP1-F | GCCTAAGGAACGGAAATTTGC | 200 |
|  | 8 | TIMP1-R | AGCCCACGAGGACCTGATC |  |

The results of this example are shown in FIGS. 1 to 4. FIG. 1 is a schematic diagram showing the effect of the *Lactobacillus plantarum* strain TCI227 of the present invention on regulating the expression of the IL-1β gene. As shown in FIG. 1, compared with the blank control group, the expression ratio of IL-1β gene in the pathological control group was significantly increased, which indicated that uric acid crystals caused inflammatory reaction of mouse chondrocytes; compared with the pathological control group, the expression ratio of IL-1β gene in the experimental group was significantly reduced (87% reduction).

Figure 2:
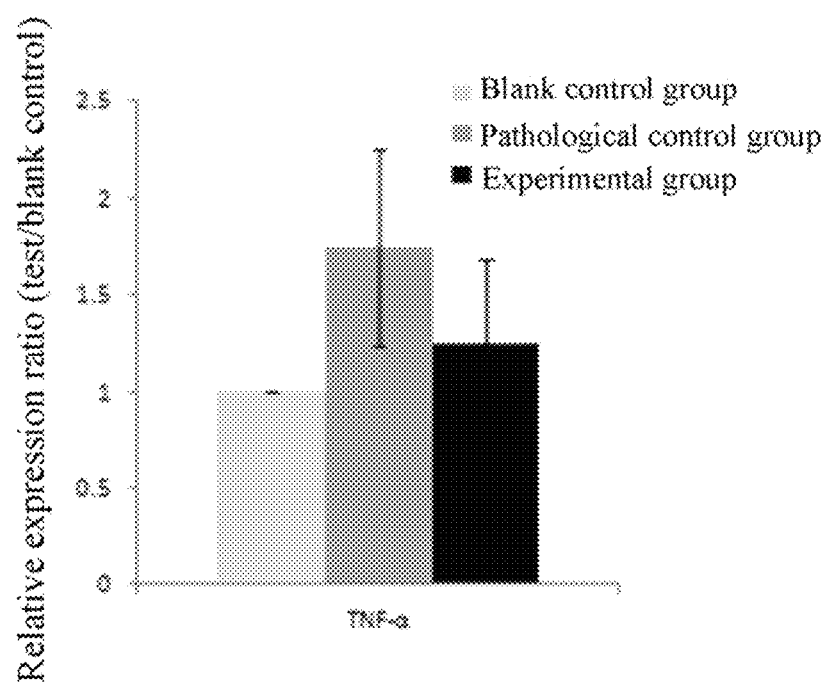
FIG. 2 is a schematic diagram showing the effect of the *Lactobacillus plantarum* strain TCI227 of the present invention on regulating the expression of the TNF-α gene.

FIG. 2 is a schematic diagram showing the effect of the *Lactobacillus plantarum* strain TCI227 of the present invention on regulating the expression of the TNF-α gene. As shown in FIG. 2, compared with the blank control group, the expression ratio of TNF-α gene in the pathological control group was significantly increased, which indicated that uric acid crystals caused inflammatory reaction of mouse chondrocytes; compared with the pathological control group, the expression ratio of TNF-α gene in the experimental group was significantly reduced (28% reduction).

Figure 3:
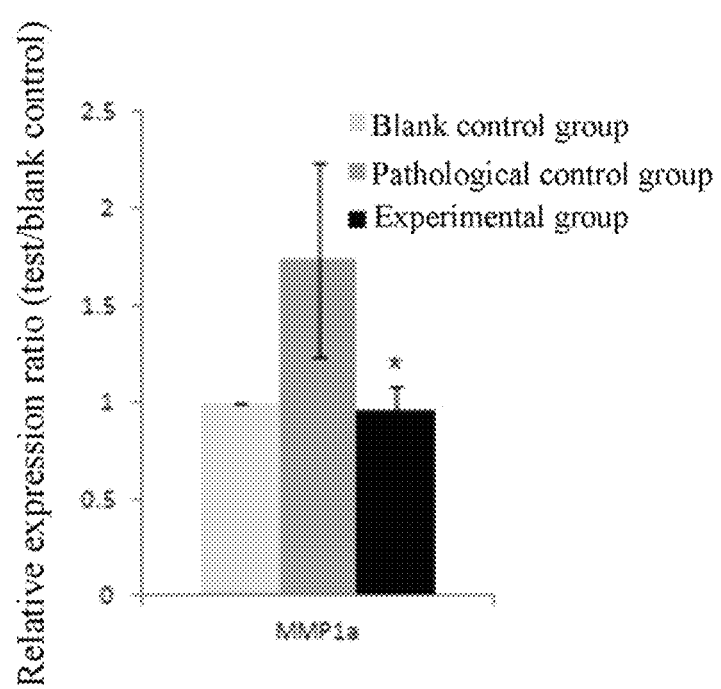
FIG. 3 is a schematic diagram showing the effect of the *Lactobacillus plantarum* strain TCI227 of the present invention on regulating the expression of the MMP1a gene, wherein "*" indicates when compared with the pathological control group, $p<0.05$.

FIG. 3 is a schematic diagram showing the effect of the *Lactobacillus plantarum* strain TCI227 of the present invention on regulating the expression of the MMP1a gene. Overexpression of the MMP1a gene causes diseases such as arthritis. As shown in FIG. 3, compared with the blank control group, the expression ratio of MMP1a gene in the pathological control group was significantly increased, which indicated that uric acid crystals caused inflammatory reaction of mouse chondrocytes; compared with the pathological control group, the expression ratio of MMP1a gene in the experimental group was significantly reduced (43% reduction).

Figure 4:
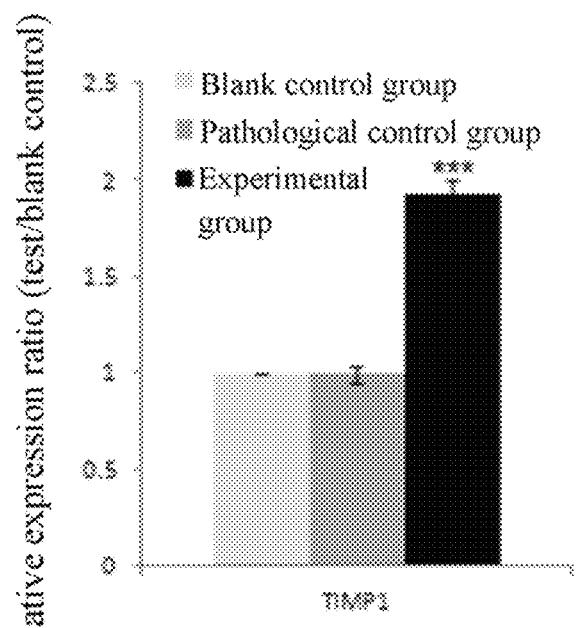
FIG. 4 is a schematic diagram showing the effect of the *Lactobacillus plantarum* strain TCI227 of the present invention on regulating the expression of the TIMP1 gene, wherein "***" indicates when compared with the pathological control group, $p<0.001$.

FIG. 4 is a schematic diagram showing the effect of the *Lactobacillus plantarum* strain TCI227 of the present invention on regulating the expression of the TIMP1 gene. The TIMP1 gene inhibits MMPs gene expression. As shown in FIG. 4, compared with the blank control group and the pathological control group, the expression ratio of TIMP1 gene in the experimental group was significantly increased (83% increase). The result of this example shows that the *Lactobacillus plantarum* strain TCI227 of the present invention can effectively reduce the immune and inflammatory reaction induced by uric acid crystals, thereby achieving the effect of treating gout.

Example 2

Evaluation of Effect of *Lactobacillus Plantarum* Strain TCI227 on Treating Gout in Human Trials In this example, it was investigated whether the *Lactobacillus plantarum* strain TCI227 of the present invention can treat gout by human trials. First, three gout patients were recruited. The condition of the subjects was high uric acid and a medical history of gout. Each gout patient was orally administered with the *Lactobacillus plantarum* strain TCI227 (in capsule form, at a dose of $1 \times 10^{10}$ cells/day). One capsule was taken daily and the blood uric acid value was examined before administration, 4 weeks and 8 weeks after administration. The experimental result is shown in FIG. 5.

Figure 5:
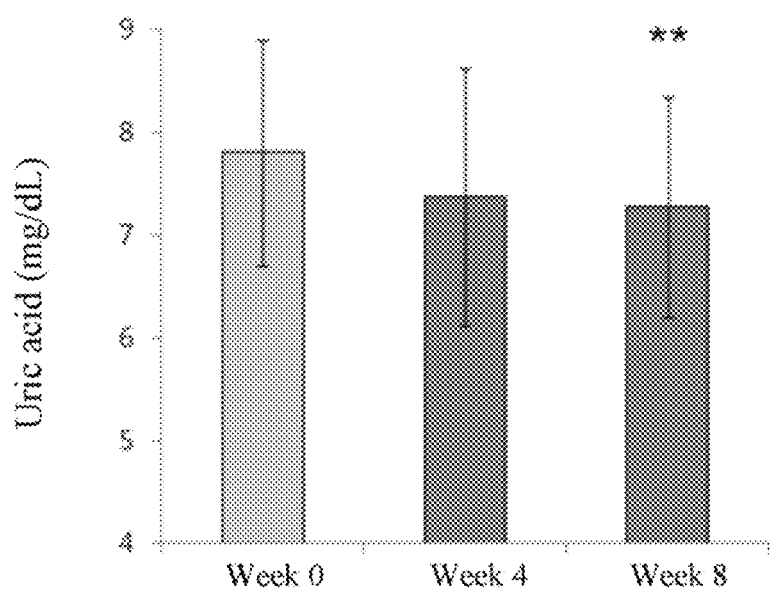
FIG. 5 is a schematic diagram showing the effect of the *Lactobacillus plantarum* strain TCI227 of the present invention on treating gout in a human test, wherein "**" indicates when compared with week 0, $p<0.01$.

FIG. 5 is a schematic diagram showing the effect of the *Lactobacillus plantarum* strain TCI227 of the present invention on treating gout in a human test. As shown in FIG. 5, after taking the capsules containing the *Lactobacillus plantarum* strain TCI227 for 4 weeks and 8 weeks, the uric acid value was significantly lowered than that before administration (week 0) (6.8% reduction at week 8, i.e., 0.53 mg/dL). The result of the experiment shows that the *Lactobacillus plantarum* strain TCI227 can achieve the effect of treating gout by reducing the uric acid value of gout patients.

Figure 6:
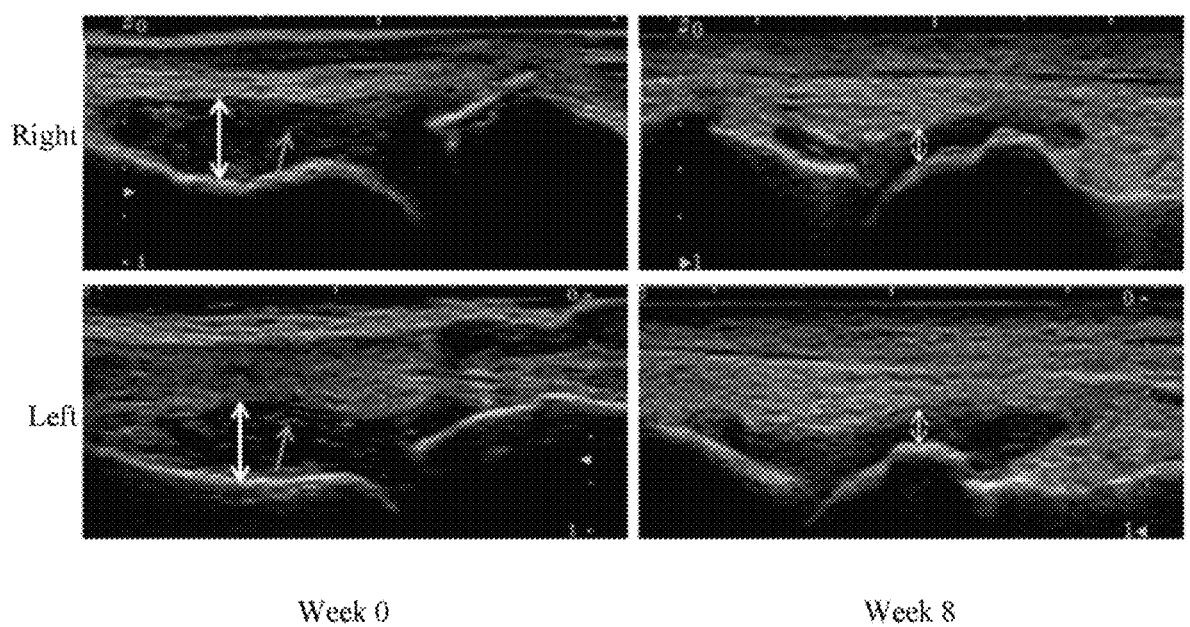
FIG. 6 is a sonogram showing the effect of the *Lactobacillus plantarum* strain TCI227 of the present invention on treating gout in a human test.

In addition, skeletal muscle ultrasound observation was performed on the gout patients before and after 8 weeks of taking the *Lactobacillus plantarum* strain TCI227, and the result is shown in FIG. 6. FIG. 6 is a sonogram showing the effect of the *Lactobacillus plantarum* strain TCI227 of the present invention on treating gout in a human test. As shown in FIG. 6, compared with before taking the capsule containing the *Lactobacillus plantarum* strain TCI227 (week 0), the degree of swelling of the joint cavity in the gout patients after taking the capsule containing the *Lactobacillus plantarum* strain TCI227 for 8 weeks was decreased, and the amount of uric acid crystals (the small white spot pointed by the gray arrow is the uric acid crystal) was also decreased. The result of the experiment shows that the *Lactobacillus plantarum* strain TCI227 can alleviate the swelling of the joint cavity caused by uric acid, thereby achieving the effect on treating gout.

In summary, the *Lactobacillus plantarum* strain has the effect on reducing the inflammatory reaction caused by uric acid crystals, lowering uric acid value, reducing the degree of joint swelling, and regulating expressions of IL-1β gene, MMP1a gene, and TIMP1 gene of chondrocytes.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for reducing inflammation of chondrocytes caused by uric acid crystals, comprising administering to a subject in need thereof a composition comprising an effective amount of *Lactobacillus plantarum* TCI227 deposited in Deutsche Sammlung von Mikrooruanismen and Zellkulturen under an accession number of DSM 33287.

2. The method according to claim 1, wherein the *Lactobacillus plantarum* TCI227 down-regulates expression of IL-1β gene and MMP1a gene and upregulates expression of TIMP1 gene to achieve the reduction of inflammation of chondrocytes caused by uric acid crystals.

3. The method according to claim 1, wherein the effective amount of the *Lactobacillus plantarum* TCI 227 is at least $5 \times 10^8$ cells/mL.

4. The method according to claim 1, wherein the *Lactobacillus plantarum* TCI227 comprises an inactivated bacterium.

5. The method according to claim 1, wherein the composition is a medicament or a food product.

* * * * *